United States Patent [19]

Gaskin

[11] Patent Number: 5,720,432
[45] Date of Patent: Feb. 24, 1998

[54] PACKAGED SHOE DEODORANT INSERT

[76] Inventor: Joan McDoom Gaskin, 2721 Columbus Cir., Charlotte, N.C. 28208

[21] Appl. No.: 560,030

[22] Filed: Nov. 17, 1995

[51] Int. Cl.$^6$ .................................................. A61L 9/04
[52] U.S. Cl. .......................................... 239/36; 239/57
[58] Field of Search ............................ 239/34, 36, 56, 239/57, 60; 36/3 B, 3 R, 43, 44

[56] References Cited

U.S. PATENT DOCUMENTS

| | | | |
|---|---|---|---|
| 2,124,396 | 7/1938 | Frank | 239/36 |
| 4,186,499 | 2/1980 | Massok et al. | 36/44 |
| 4,277,024 | 7/1981 | Spector | 239/56 X |
| 4,345,716 | 8/1982 | Armstrong et al. | 239/56 |
| 4,605,165 | 8/1986 | Van Loveren et al. | 239/56 X |
| 4,973,448 | 11/1990 | Carlson et al. | 239/34 X |
| 5,399,404 | 3/1995 | Laughlin et al. | 239/36 X |

*Primary Examiner*—Lesley D. Morris

[57] ABSTRACT

An insert for absorbing and masking odor within a shoe. The inventive device includes a joined pouch having a deodorant disinfectant material positioned therein. The joined pouch can be separated into individual pouches positionable into a pair of shoes to reduce or eliminate odor emanating therefrom.

1 Claim, 3 Drawing Sheets

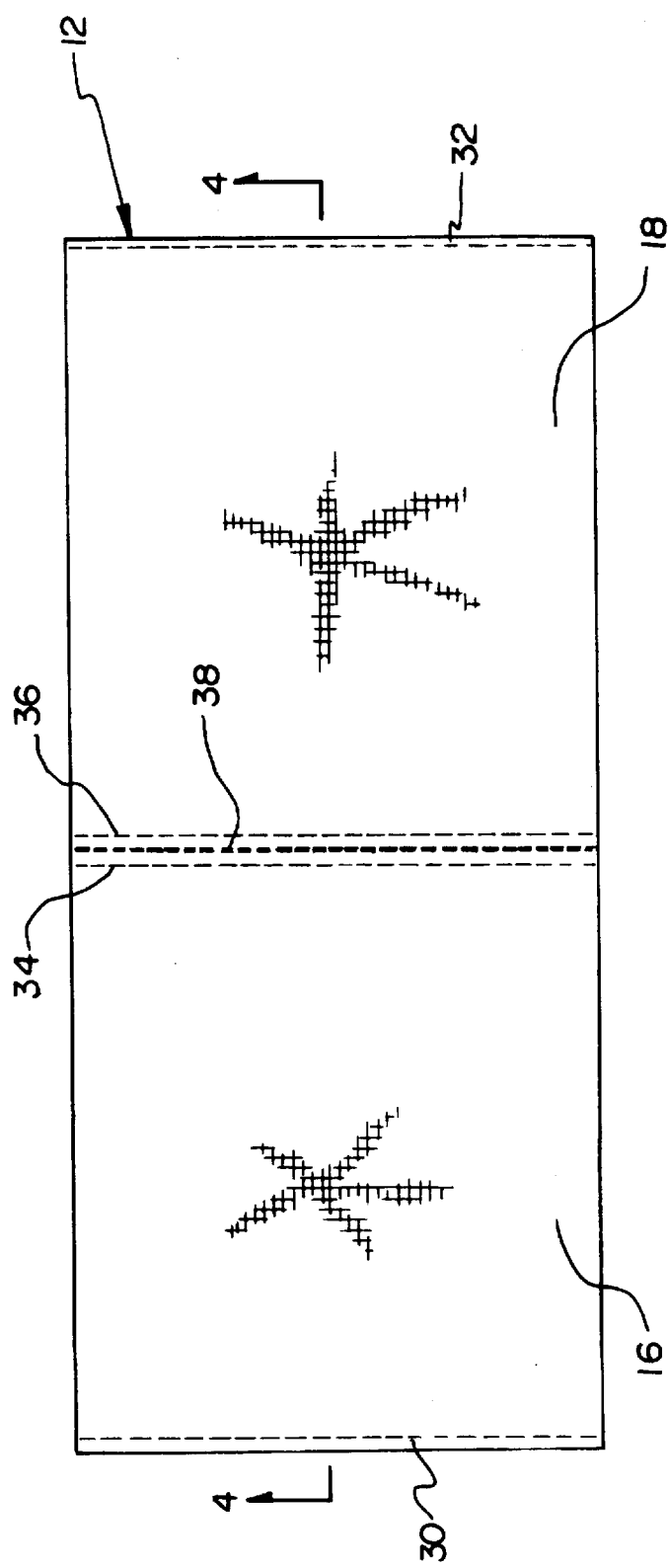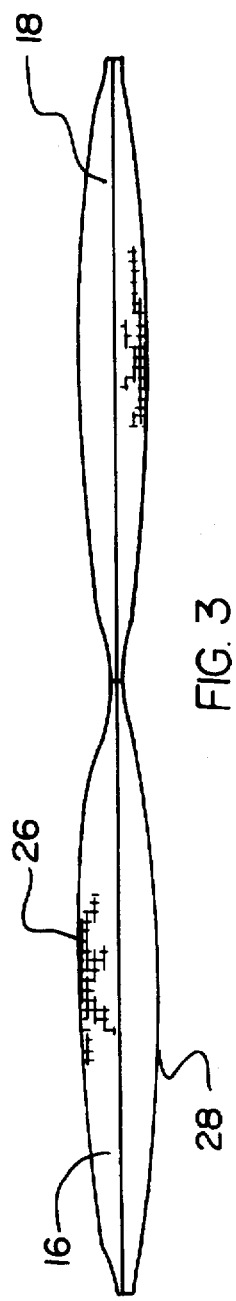

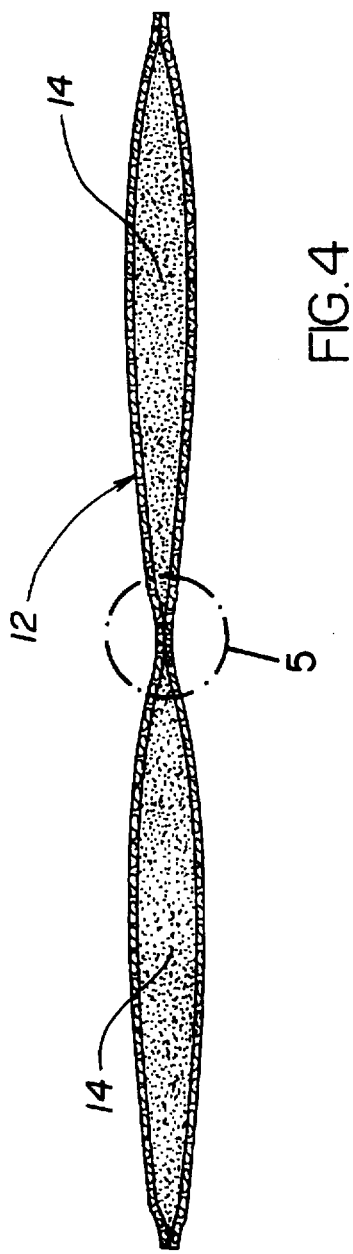
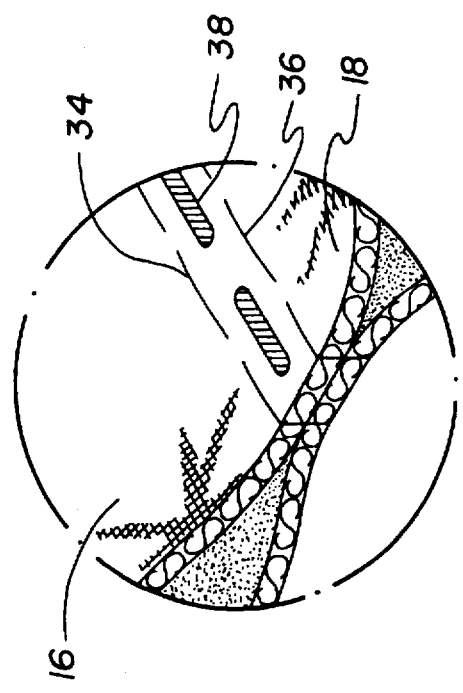

PACKAGED SHOE DEODORANT INSERT

BACKGROUND OF THE INVENTION

1. Field of the Invention

The present invention relates to deodorant devices and more particularly pertains to a packaged shoe deodorant insert for absorbing and masking odor within a shoe.

2. Description of the Prior Art

The use of deodorant devices is known in the prior art. More specifically, deodorant devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art deodorant devices include U.S. Pat. No. 4,461,099; U.S. Pat. No. 5,154,960; U.S. Pat. No. 4,998,984; U.S. Pat. No. 5,216,825; U.S. Pat. No. 5,071,628; and U.S. Pat. No. 4,575,891.

While these devices fulfill their respective, particular objectives and requirements, the aforementioned patents do not disclose a packaged shoe deodorant insert for absorbing and masking odor within a shoe which includes a joined pouch having a deodorant disinfectant material positioned therein, wherein the joined pouch cart be separated into individual pouches positionable into a pair of shoes to reduce or eliminate odor emanating therefrom.

In these respects, the packaged shoe deodorant insert according to the present invention substantially departs from the conventional concepts and designs of the prior art, and in so doing provides an apparatus primarily developed for the purpose of absorbing and masking odor within a shoe.

SUMMARY OF THE INVENTION

In view of the foregoing disadvantages inherent in the known types of deodorant devices now present in the prior art, the present invention provides a new packaged shoe deodorant insert construction wherein the same can be utilized for absorbing and masking odor within a shoe. As such, the general purpose of the present invention, which will be described subsequently in greater detail, is to provide a new packaged shoe deodorant insert apparatus and method which has many of the advantages of the deodorant devices mentioned heretofore and many novel features that result in a packaged shoe deodorant insert which is not anticipated, rendered obvious, suggested, or even implied by any of the prior art deodorant devices, either alone or in any combination thereof.

To attain this, the present invention generally comprises an insert for absorbing and masking odor within a shoe. The inventive device includes a joined pouch having a deodorant disinfectant material positioned therein. The joined pouch can be separated into individual pouches positionable into a pair of shoes to reduce or eliminate odor emanating therefrom.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new packaged shoe deodorant insert apparatus and method which has many of the advantages of the deodorant devices mentioned heretofore and many novel features that result in a packaged shoe deodorant insert which is not anticipated, rendered obvious, suggested, or even implied by any of the prior art tool guides, either alone or in any combination thereof.

It is another object of the present invention to provide a new packaged shoe deodorant insert which may be easily and efficiently manufactured and marketed.

It is a further object of the present invention to provide a new packaged shoe deodorant insert which is of a durable and reliable construction.

An even further object of the present invention is to provide a new packaged shoe deodorant insert which is susceptible of a low cost of manufacture with regard to both materials and labor, and which accordingly is then susceptible of low prices of sale to the consuming public, thereby making such packaged shoe deodorant inserts economically available to the buying public.

Still yet another object of the present invention is to provide a new packaged shoe deodorant insert which provides in the apparatuses and methods of the prior art some of the advantages thereof, while simultaneously overcoming some of the disadvantages normally associated therewith.

Still another object of the present invention is to provide a new packaged shoe deodorant insert for absorbing and masking odor within a shoe.

Yet another object of the present invention is to provide a new packaged shoe deodorant insert which includes a joined pouch having a deodorant disinfectant material positioned therein, wherein the joined pouch can be separated into individual pouches positionable into a pair of shoes to reduce or eliminate odor emanating therefrom.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a top plan view of the invention.

FIG. 3 is a front elevation thereof.

FIG. 4 is a cross sectional view taken along line 4—4 of FIG. 2.

FIG. 5 is an isometric illustration of the area set forth in FIG. 4.

DESCRIPTION OF THE PREFERRED EMBODIMENT

Figure 1:
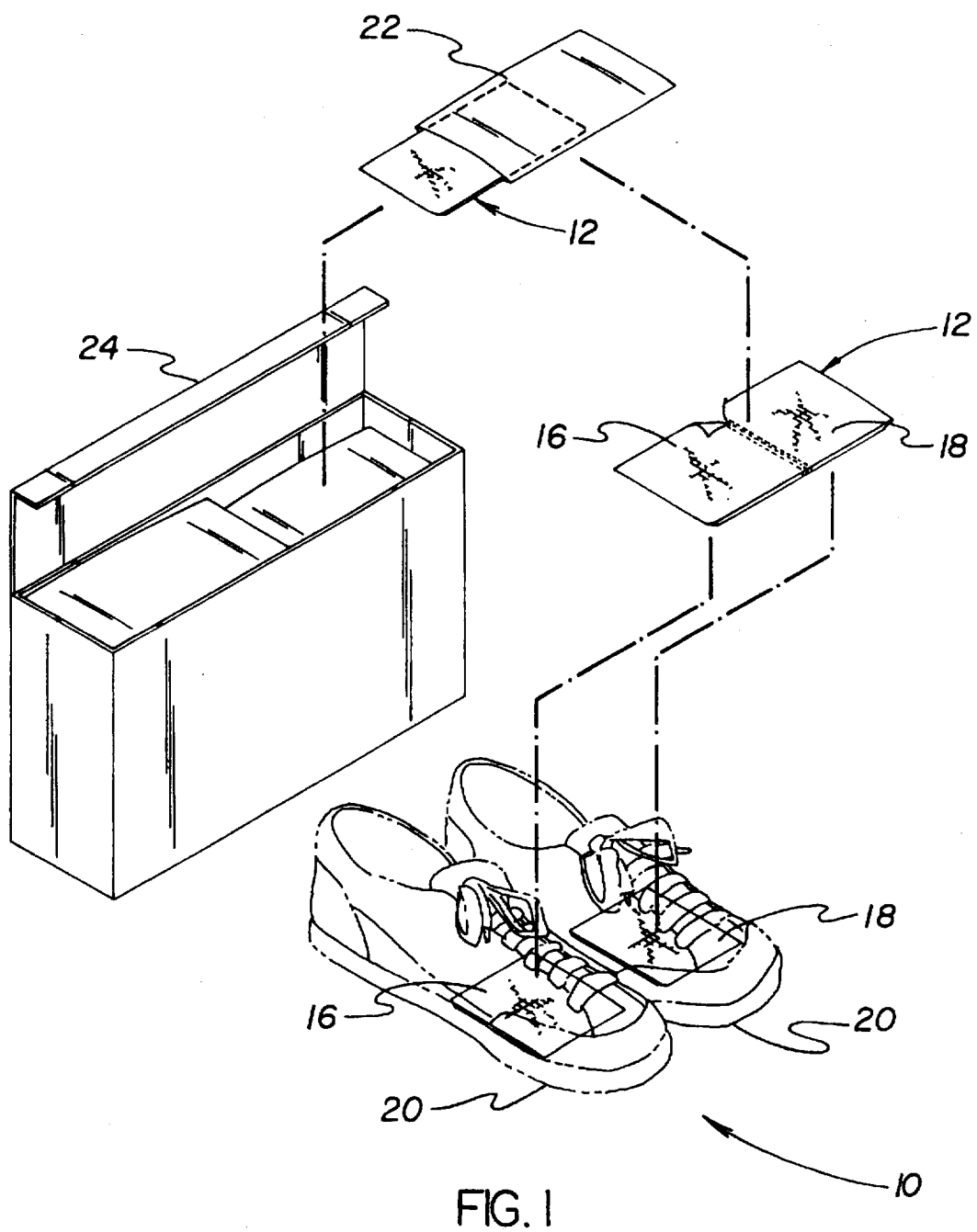
FIG. 1 is an exploded isometric illustration of a package shoe deodorant insert according to the present invention.

With reference now to the drawings, and in particular to FIGS. 1-5 thereof, a new packaged shoe deodorant insert embodying the principles and concepts of the present invention and generally designated by the reference numeral 10 will be described.

More specifically, it will be noted that the packaged shoe deodorant insert 10 comprises a joined pouch 12 having a deodorant disinfectant material 14 (see FIG. 4) which operates to absorb and/or mask airborne odors. The joined pouch 12, as shown in FIG. 1, can be separated along a medial portion thereof into a first individual pouch 16 and a second individual pouch 18. The individual pouches 16 and 18 can then be each positioned into an individual one of a pair of shoes 20 so as to absorb and mask odors emanating from the shoes. Preferably, the joined pouch 12 is initially stored within a storage envelope 22 and sealed therewithin so as to protect the deodorant disinfectant material 14 prior to use of the invention. A container 24 can be provided for supplying a plurality of the joined pouches 12 each positioned within an individual storage envelope 22 for convenient dispensing and use by an individual as described above.

Referring now to FIGS. 2 through 5 wherein the present invention 10 is illustrated in detail, it can be shown that the joined pouch 12 of the present invention 10 preferably comprises a spirally woven fabric cylinder which has been flattened so as to define an upper web portion 26 spaced from a lower web portion 28. A first end seam 30 extends along a first end of the fabric cylinder so as to couple the upper web portion 26 to the lower web portion 28. Similarly, a second end seam 32 extends along a second end of the fabric cylinder to join the upper portion 26 to the lower web portion 28. Further, first and second center seams 34 and 36 extend in a substantially spaced and parallel orientation across a medial portion of the fabric cylinder to join the upper web portion 26 to the lower web portion 28 thereof. The seams 30-36 may comprise adhesive seams, but preferably comprise stitched seams utilizing an interwoven thread substantially as shown in FIG. 2 of the drawings. By this structure, the joined pouch 12 is shaped so as to define unlabeled first and second interior spaces wherein the deodorant disinfectant material 14 is positioned. To permit separation of the first individual pouch 16 from the second individual pouch 18 of the joined pouch 12, a perforated area 38 extends transversely across the fabric cylinder between the center seams 34 and 36. To this end, the perforated area 38 comprises a plurality of apertures directed through both the upper web portion 26 and the lower web portion 28 which extend in a linear orientation between the center seams 34 and 36 substantially as shown in FIG. 5 of the drawings. By this structure, the first individual pouch 16 can be frangibly separated from the second individual pouch 18 by a tearing separation of the fabric cylinder along the medial portion thereof between the center seams 34 and 36.

The deodorant disinfectant material 14 illustrated in FIG. 4 of the drawings may comprise any conventionally known deodorant and/or disinfectant material such as activated charcoal, baking powder, or other known air freshening compositions.

In use, the packaged shoe deodorant insert 10 according to the present invention can be easily utilized for absorbing and masking odor within a pair of shoes 20. A method of use of the present invention includes providing a joined pouch 12 positioned within a storage envelope 22, wherein the joined pouch 12 includes a first individual pouch 16 coupled to a second individual pouch 18 with the individual pouches 16 and 18 each including and containing a deodorant disinfectant material 14 positioned therein. The method continues by separating the first individual pouch 16 from the second individual pouch 18 and subsequently positioning the first individual pouch within a first one of a pair of shoes 20, and positioning the second individual pouch 18 within a second one of a pair of shoes. The method may further comprise providing the joined pouch 12 within a storage envelope 22, and subsequently removing the joined pouch 12 from the storage envelope 22 prior to separation of the first individual pouch 16 from the second individual pouch 18. The method may further additionally comprise providing a plurality of joined pouches 12 each stored within an individual storage envelope 22 and positioned within a container 24. By this structure and method, a pair of shoes 20 can be disinfected and deodorized during periods of non-use and/or use of the shoes.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A packaged shoe deodorant insert comprising:

a joined pouch having a deodorant disinfectant material positioned therein which operates to absorb and mask airborne odors, the joined pouch being separable along a medial portion thereof into a first individual pouch and a second individual pouch, the joined pouch having a spirally woven fabric cylinder which has been flattened so as to define an upper web portion spaced from a lower web portion, a first end seam extending along a first end of the fabric cylinder so as to couple a first end of the upper web portion to a first end of the lower web portion, a second end seam extending along a second end of the fabric cylinder so as to couple a second end of the upper web portion to a second end of the lower web portion, first and second center seams extending in a substantially spaced and parallel orientation across a medial portion of the fabric cylinder to join medial portions of the upper web portion and the lower web portion together, the seams of the joined pouch cooperating to define first and second interior spaces wherein the deodorant disinfectant material is positioned, and a perforated area extending transversely across the fabric cylinder between the center seams, the individual pouches each being positionable into an individual one of a pair of shoes so as to absorb and mask odors emanating from the shoes;

the perforated area comprises a plurality of apertures directed through both the upper web portion and the lower web portion which extend in a linear orientation between the center seams such that the first individual pouch can be frangibly separated from the second individual pouch by a tearing separation of the fabric cylinder along a medial portion thereof between the center seams;

a storage envelope for allowing the joined pouch to be initially stored therein for protection of the deodorant disinfectant material prior to use; and a container, with the storage envelop and joined pouch positioned therewithin being positioned within the container.

* * * * *